(12) United States Patent
Bardon et al.

(10) Patent No.: US 6,649,601 B2
(45) Date of Patent: *Nov. 18, 2003

(54) PROCESS FOR INCREASING THE EGG PRODUCTION AND STRENGTHENING THE EGGSHELLS OF POULTRY

(75) Inventors: Thierry Bardon, Bouliac (FR); Dominique Thibaud, Gujan Mestras (FR)

(73) Assignee: Ceva Sante Animale, Libourne (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/506,032

(22) Filed: Feb. 17, 2000

(65) Prior Publication Data

US 2003/0013685 A1 Jan. 16, 2003

(30) Foreign Application Priority Data

Jan. 12, 2000 (FR) .............................. 00 00354

(51) Int. Cl.⁷ ........................ A61K 31/675; A61K 31/66
(52) U.S. Cl. ......................................... 514/89; 514/108
(58) Field of Search ................................... 514/89, 108

(56) References Cited

U.S. PATENT DOCUMENTS 5,488,041 A * 1/1996 Barbier et al. .............. 514/108

OTHER PUBLICATIONS

Oderkirk A., The Role of Calcium Phosphorus and Vitamin D3 in Egg Shell and Bone Formation, Poultry Fact Sheet, Department of Agriculture and Fisheries, Province of Novia Scotia, 1998.*

Wilson, S., et al.: "*Bisphosphonates: a potential role in the prevention of osteoporosis in laying hens,*" Research in Veterinary Science, vol. 64, No. 1, 1998, pp. 37–40.

Thorp, B.H., "*The effect of a bisphosphonate on bone volume and eggshell structure in the hen,*" Avian Pathology, vol. 22, No. 4, 1993, pp. 671–682.

* cited by examiner

Primary Examiner—Sreeni Padmanabhan
Assistant Examiner—San-ming Hui
(74) Attorney, Agent, or Firm—Jacobson Holman PLLC

(57) ABSTRACT

The present invention relates to a process for increasing the egg production and strengthening the eggshells of poultry, which comprises the administration to the animal of at least one bisphosphonic compound chosen from a bisphosphonic acid, a physiologically acceptable salt thereof, hydrates thereof and mixtures thereof.

9 Claims, No Drawings

PROCESS FOR INCREASING THE EGG PRODUCTION AND STRENGTHENING THE EGGSHELLS OF POULTRY

The invention relates to a process for increasing the egg production and strengthening the eggshells of poultry.

The invention moreover relates to a process for manufacturing preparations which can be administered to poultry for increasing egg production and strengthening the shells.

The process of the invention consists in administering at least one bisphosphonic acid or a physiologically acceptable salt thereof.

Among the species which produce eggs for consumption, the hen is by far the main species. Constant progress in the fields of genetic selection and nutrition have led over the last 30 years to a steady increase in the number of eggs laid per hen. It is now common for a hen to lay more than 300 eggs in a laying year, which corresponds, in the most productive phase of the laying period, to one egg laid per day. Paradoxically, this change is accompanied by a reduction in the size of the animals and thus, in particular, in the volume of the calcium reserve represented by the skeleton. This reserve is essential for producing a good-quality shell. The decrease in the calcium available in the body to produce the shell has as a first consequence the production of more fragile shells which have defects in the organic mineralized frame. Secondly, if the phenomenon persists, the laying of the egg itself is compromised.

Bisphosphonic acid derivatives of medical interest are nowadays well known. Their pharmacological properties and their therapeutic applications are well described in the prior art in the case of mammals, in particular man. On account of their anti-resorptive properties on bone and their regulatory action on bone remodelling, bisphosphonic acid derivatives nowadays form part of the therapeutic arsenal available to medical practitioners for treating pathologies in man which are associated with disruptions in bone metabolism, such as osteoporosis, Paget's disease or malignant hypercalcaemias.

Conversely, few investigations have been carried out to date on birds. It appears that, in birds, bisphosphonic acid derivatives also exert their property of inhibiting bone resorption. Specifically, investigations carried out with alendronate (or [4-amino-1-hydroxybutylidene] bisphosphonate) in laying hens demonstrated the ability of this compound to limit bone resorption.

A first study reports the inhibitory effect of alendronate on the bone resorption which accompanies the acquisition of sexual maturity in laying hens when the product is administered subcutaneously at a dose of 0.01 mg/kg twice a week from the 16-week-old stage and up to the laying of the first egg (cf. Thorp B. H. et al., 1993, *Avian Pathol.*, 22, 671–682).

A second study uses a slightly different administration protocol: alendronate is administered via the same route at a dose of 0.01 mg/kg at a rate of 6 administrations in total spread over 2 weeks from the 14-week-old stage (cf. Wilson S. et al., *Res. Vet. Sci.*, 1998, 64, 37–40). As in the previous study, this study demonstrates the inhibitory effect of alendronate on the bone resorption which precedes the laying of the first egg.

The studies reported above indicate that alendronate did not bring about any change in the age of onset of laying.

The use of compounds which can reduce the calcium mobilization required to produce the eggshell appears to be detrimental both as regards the production of good-quality shells and as regards the production of eggs. Due to their anti-resorptive action, bisphosphonic acid derivatives should in principle exert such detrimental effects.

In the two studies reported above, it was shown that the volume of the medullary bone is substantially lower in hens receiving alendronate compared with control hens, irrespective of the time of administration of the compound, i.e. before the onset of laying or during laying. Medullary bone is a bone which is specific to female birds; this bone acts as a calcium reservoir required to constitute the eggshell. At each cycle of laying, this bone undergoes a partial resorption allowing the release of calcium, followed by a new mineralization which is exploited in the next cycle. The results obtained regarding the decrease in medullary bone volume in the studies cited above thus suggest that the administration of bisphosphonic acid derivatives before the onset of laying or during laying is liable to compromise the mineralization of the eggshell and, consequently, the quality of the eggshell.

The study by Thorp et al. moreover demonstrates that the administration of alendronate during laying at doses of 0.01, 0.1 or 1 mg/kg can lead to a reduction, or even the stopping, of laying. Thus, the injection of a dose of 1 mg/kg subcutaneously every 2 days for 2 weeks, about 18 weeks after the onset of laying, brings about a complete stoppage of laying within a few days. Furthermore, the product is the cause of an adverse change in the quality of the shell, which is all the more pronounced the higher the dose.

Now, the present inventors have discovered, surprisingly, that compounds of bisphosphonate type are useful for increasing the production of eggs in poultry as well as for improving the quality of the shell of the eggs laid.

More specifically, the invention relates to a process for increasing the egg production and the strengthening eggshells of poultry, which comprises the administration to the animal of at least one bisphosphonic compound chosen from a bisphosphonic acid, a physiologically acceptable salt thereof, hydrates thereof and mixtures thereof.

The expression "bisphosphonic acid and salt of this acid" generally means a compound which has a P—C—P linkage.

The salts of this compound with pharmaceutically acceptable inorganic or organic acids or bases can also be used in the context of the invention. Examples of salts with acids are the hydrochloride, hydrobromide, sulphate, acetate, hydrogen sulphate, dihydrogen phosphate, methanesulphonate, methyl sulphate, maleate, fumarate, sulphonate, 2-naphthalenesulphonate, glycolate, gluconate, citrate, isethionate, benzoate, salicylate, tartrate, succinate, lactate, glutarate, toluene-sulphonate and ascorbate salts. Examples of salts with inorganic or organic bases which may be mentioned are the ammonium salts or the salts of alkali metals such as, for example, the sodium salts.

The hydrates of these compounds can similarly be used according to the invention.

The compounds of bisphosphonic type described in the prior art as promoting bone resorption or recommended in the treatment of Paget's disease can be used in the context of the invention. More generally, the bisphosphonic acids and the salts of these acids described in the following patent applications fall within the context of the definition of bisphosphonic compounds which can be administered according to the invention: WO 87/03598, EP 325 482, BE 822 930; EP 304 961; U.S. Pat. No. 4,621,077; FR 2 826 223; WO 86/00902; EP 162 510; EP 186 405; U.S. Pat. No. 4,922,007; U.S. Pat. No. 4,578,376; BE 865 434; U.S. Pat. No. 4,134,969; DE 2 130 794 and BE 902 308.

In general, the bisphosphonic compound has the formula:

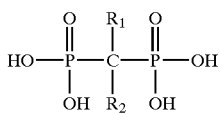

I in which $R_1$ and $R_2$ are, independently, a hydrogen atom; a halogen atom; a hydroxyl group; a group —T; or a group —XT;

T is chosen from an aliphatic saturated or unsaturated hydrocarbon-based radical, optionally substituted and/or optionally interrupted with one or more O, S, N, N—CO, CO—N, CO, SO or $SO_2$; a saturated, unsaturated or aromatic, optionally substituted carbocyclic or heterocyclic radical; a radical with both an aliphatic part as defined above and a carbocyclic and/or heterocyclic part as defined above, the said radical being optionally substituted and/or optionally interrupted with one or more O, S, N, N—CO, CO—N, CO, SO or $SO_2$;

X is chosen from O, NH, NT, S, CO, CO—NT and NT—CO, in which T is as defined above;

or is a physiologically acceptable salt of this compound, or alternatively a hydrate thereof.

The expression "aliphatic radical" means a non-cyclic hydrocarbon-based radical such as alkyl, alkenyl and alkynyl, the latter groups being unsaturated one or more times.

Examples of alkyl groups are methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methyl-pentyl, 1,1-dimethylbutyl, 1,3-dimethylbutyl, 2-ethyl-butyl, 1-methyl-1-ethylpropyl, heptyl, 1-methylhexyl, 1-propylbutyl, 4,4-dimethylpentyl, octyl, 1-methyl-heptyl, 2-ethylhexyl, 5,5-dimethylhexyl, nonyl, decyl, 1-methylnonyl, 3,7-dimethyloctyl and 7,7-dimethyloctyl.

The alkyl radicals can contain up to 25 carbon atoms. They preferably contain from 1 to 12 carbon atoms, better still from 1 to 6 carbon atoms.

The alkenyl and alkynyl groups can contain up to 25 carbon atoms. They preferably comprise from 2 to 12 carbon atoms, better still from 2 to 6 carbon atoms.

The expression "carbocyclic radical" means a monocyclic or polycyclic, preferably monocyclic or bicyclic, hydrocarbon-based radical. Generally, this radical comprises 3 to 18 carbon atoms (for example from 3 to 10).

Such saturated or unsaturated radicals are, for example, cycloalkyl and cycloalkenyl. Cycloalkenyl can comprise one or more unsaturations. Examples of cycloalkyl are cyclopentyl, cyclohexyl, cycloheptyl, cyclooctyl, adamantyl and norbornyl.

The aromatic carbocyclic radicals are, for example, mono- or bicyclic, preferably $C_6-C_{18}$ aryl radicals.

Examples of these are phenyl, naphthyl, anthryl and phenanthryl radicals, more preferably phenyl.

The expression "heterocyclic radical" means monocyclic or polycyclic, preferably monocyclic or bicyclic, radicals comprising one or more hetero atoms chosen from O, N and S. These radicals consist of cyclic nuclei fused two-to-two or linked, two-to-two, via sigma bonds, each nucleus containing or not containing one or more unsaturations and preferably containing 5 to 10, better still from 5 to 8, ring members. Aromatic heterocyclic radicals and saturated and unsaturated heterocyclic radicals are distinguished.

Preferably, the heterocyclic radical comprises 1, 2, 3 or 4 hetero atoms chosen from O, N and S.

Examples of these are pyrrolidine, dioxolane, imidazolidine, pyrazolidine, piperidine, dioxane, morpholine, dithiane, thiomorpholine, piperazine, trithiane, indoline, indene, carbazole, phenothiazine, phenoxazine and fluorene radicals, saturated, unsaturated and aromatic derivatives thereof, as well as the heteroaryls defined below: furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrazinyl, triazinyl, indolizinyl, indolyl, isoindolyl, benzofuryl, benzothienyl, indazolyl, benzimidazolyl, benzothiazolyl, purinyl, quinolizinyl, quinolyl, isoquinolyl, cinnolinyl, phthalazinyl, quinazolinyl, quinoxalinyl, naphthyridinyl, pteridinyl, acridinyl, phenazinyl, and saturated or unsaturated derivatives thereof.

Radicals containing both an aliphatic part and a carbocyclic and/or heterocyclic part advantageously have the formula -alk-Ar in which alk is alkyl, preferably $C_1-C_{12}$, and Ar represents $(C_1-C_{18})$aryl or mono-, bi- or tricyclic heteroaryl containing from 1 to 4 hetero atoms chosen from O, N and S. A preferred example of such a radical is benzyl.

When Ar represents heteroaryl, it is preferably chosen from the heteroaryls listed above.

The term "halogen atom" generally means a chlorine, bromine, iodine or fluorine atom.

When an aliphatic radical is interrupted with N, N—CO and CO—N, the nitrogen atom also bears a hydrogen atom or an aliphatic radical as defined above for T. When the radical interrupted with N, N—CO or CO—N is a radical containing both an aliphatic part and a heterocyclic or carbocyclic part, the nitrogen atom bears a carbocyclic or heterocyclic radical, or an aliphatic radical or else a hydrogen atom.

Preferably, X is chosen from O, S, NH and NT, better still from O and S.

According to the invention, the substituents on the radical representing T is not critical. It is generally a monovalent organic group. Preferred substituents which may be mentioned are —OH, SH and —$NH_2$ groups and halogen atoms.

Advantageously, T is chosen from $(C_1-C_{12})$alkyl optionally substituted with one or more groups K as defined below; mono-, bi- or tricyclic $(C_6-C_{18})$aryl optionally substituted with one or more groups K; mono-, bi- or tricyclic heteroaryl comprising 1, 2, 3 or 4 hetero atoms chosen from O, N and S optionally substituted with one or more groups K, and in which each monocyclic unit contains from 5 to 8 ring members; $(C_6-C_{18})$aryl $(C_1-C_{12})$alkyl optionally substituted with one or more groups K; heteroaryl$(C_1-C_{12})$alkyl optionally substituted with one or more groups K, in which heteroaryl is as defined above; monocyclic saturated heterocycle containing from 5 to 8 ring members and 1, 2, 3 or 4 hetero atoms chosen from N, S and O, optionally fused to a $(C_6-C_{18})$aryl nucleus as defined above, and optionally substituted with one or more groups K; or $(C_1-C_{12})$alkyl substituted with a saturated monocyclic heterocycle as defined above and optionally fused to a $(C_6-C_{18})$aryl and optionally substituted on the alkyl or aryl part or on the heterocyclic part with one or more groups K;

K is chosen from OH; SH; $(C_1-C_{12})$alkoxy; $(C_1-C_{12})$alkylthio; —$NH_2$; $(C_1-C_{12})$alkylamino; di$(C_1-C_{12})$alkyl-amino; and a halogen atom.

A preferred sub-group of the bisphosphonic compounds described above is that defined by formula I above in which $R_1$ represents a hydrogen atom, a halogen atom, a hydroxyl, an amino, a mono$(C_1-C_4)$alkylamino or a di$(C_1-C_4)$ alkylamino;

$R_2$ represents a halogen atom, a linear alkyl comprising from 1 to 5 carbon atoms which is unsubstituted or substituted with a group chosen from a chlorine atom, a hydroxyl, an amino, a mono($C_1$–$C_4$) alkylamino, a di($C_1$–$C_4$)alkylamino; a ($C_3$–$C_7$) cycloalkylamino, or $R_2$ represents a phenoxy, a phenyl, a thiol, a phenylthio, a chlorophenylthio, a pyridyl, a pyridylmethyl, a 1-pyridyl-1-hydroxymethyl, an imidazolylmethyl or a 4-thiomorpholinyl.

A second preferred sub-group consists of the compounds of formula I in which:

$R_1$ represents a hydrogen atom; a halogen atom; a hydroxyl group optionally substituted with a group $A_o$; a group $A_o$; an alkyl group, preferably $C_1$–$C_{12}$, optionally substituted with one or more substituents chosen independently from a halogen atom, hydroxyl, hydroxyl substituted with a group $B_o$, thiol, thiol substituted with a group $B_o$ and groups $A_o$;

$R_2$ represents a thiol group optionally substituted with $A_o$ or with an alkyl group, preferably $C_1$–$C_{12}$, itself optionally substituted with one or more substituents chosen from hydroxyl, a halogen atom, a group $A_o$ and a thiol group;

$A_o$ represents an aryl group; heteroaryl group; arylalkyl group; heteroarylalkyl group; a saturated monocyclic heterocyclic group optionally fused to a ($C_6$–$C_{18}$)aryl; or an alkyl group substituted with such a saturated monocyclic heterocyclic group optionally fused to a ($C_6$–$C_{18}$)aryl; each of these groups optionally being substituted on the aromatic or heterocyclic part or on the aliphatic part with one or more hydroxyl, halogen, alkyl (preferably $C_1$–$C_{12}$), alkoxy (preferably $C_1$–$C_{12}$) thiol or alkylthio (preferably $C_1$–$C_{12}$);

$B_o$ represents $A_o$ or alkyl, preferably $C_1$–$C_{12}$, optionally substituted with one or more groups chosen from hydroxyl, halogen, alkoxy (preferably $C_1$–$C_{12}$), thiol or alkylthio (preferably $C_1$–$C_{12}$).

In this sub-group, heterocycle, heteroaryl and aryl are generally as defined above.

Preferably, "heteroaryl" denotes pyridyl, thienyl or furyl and "aryl" represents phenyl. Preferably, "heterocycle" denotes pyrrolidine, tetrahydrofuryl, tetrahydrothienyl, piperidine or morpholine.

Among these compounds, the ones most particularly preferred are the compounds of formula I in which:

$R_1$ is a halogen atom, preferably chlorine, or a group ($C_1$–$C_{12}$)alkyl which is optionally substituted, preferably with one or more halogen atoms.

$R_2$ is a ($C_6$–$C_{12}$)arylthio or ($C_4$–$C_{10}$)heteroarylthio, each of these groups optionally being substituted, preferably with one or more thiol and/or halogen groups.

Among the bisphosphonic compounds which can be used in the context of the invention, mention may be made more specifically of:

1-hydroxyethylidenebisphosphonic acid whose international nonproprietary name is etidronic acid, and its sodium salts;

2-pyrid-2-ylethylidenebisphosphonic acid, the international nonproprietary name of which is piridronic acid, and its sodium salts;

dichloromethylenebisphosphonic acid, the international nonproprietary name of which is clodronic acid, and its sodium salts;

3-amino-1-hydroxypropylidenebisphosphonic acid, the international nonproprietary name of which is pamidronic acid, and its sodium salts;

3-(dimethylamino)-1-hydroxypropylidenebisphosphonic acid, the international nonproprietary name of which is olpadronic acid, and its salts;

1-hydroxy-3-(methylpentylamino) propylidenebisphosphonic acid, the international nonproprietary name of which is ibandronic acid, and its salts;

4-amino-1-hydroxybutylidenebisphosphonic acid, the international nonproprietary name of which is alendronic acid, and its sodium salts;

6-amino-1-hydroxyhexylidenebisphosphonic acid, the international nonproprietary name of which is neridronic acid, and its salts;

phenoxymethylenebisphosphonic acid and its salts;

thiomorpholinomethylenebisphosphonic acid and its salts;

4-chlorophenylthiomethylenebisphosphonic acid, the international nonproprietary name of which is tiludronic acid, and its pharmaceutically acceptable salts, in particular the disodium salt;

1-hydroxy-2-(3-pyridyl)ethylidenebisphosphonic acid, the international nonproprietary name of which is risedronic acid, and its sodium salts;

1-hydroxy-2-(1H-imidazol-1-yl)ethylidenebisphosphonic acid, the international nonproprietary name of which is zoledronic acid, and its salts;

(cycloheptylamino)methylenebisphosphonic acid, the international nonproprietary name of which is incadronic acid, and its salts;

2-hydroxyethylidene-2-(3-pyridyl)-1,1-bisphosphonic acid and its sodium salts.

In general, the nitrogenous bisphosphonic compounds are distinguished from the non-nitrogenous bisphosphonic compounds, the latter being preferred.

According to the present invention, the use of tiludronic acid and its pharmaceutically acceptable salts, in particular the disodium salt, or its hydrates, is particularly preferred.

It should be understood that, according to the invention, the administration of a mixture of two or more bisphosphonic compounds can be envisaged.

The process of the invention is more specifically suitable for the administration of bisphosphonic compounds to poultry which produce eggs fit for consumption, such as hens, ducks and quails.

According to one preferred embodiment, the poultry is hens.

The route of administration can be the oral route, the parenteral route or the nasal route. Via the oral route, the treatment can be administered in drinking water. Via the parenteral route, the subcutaneous, intradermal, intramuscular, intravenous or intra-articular route can be used. Via the nasal route, the treatment can be administered by means of devices for dispersing in air fine droplets of liquid, preferably water, into which the medicinal product will have been incorporated beforehand. Such devices are, for example, nebulizers, atomizers, vaporizers or aerosols.

The pharmaceutical form of administration of the medicinal product depends on the route of administration. Via the oral route, forms which can be dissolved in drinking water are preferred. Among these, mention may be made of oral powders, fast-dissolving tablets, effervescent tablets and drinkable solutions. For the parenteral route, the treatment can be administered in the form of a solution, preferably an aqueous solution, a suspension, implants or freeze-dried preparations.

The preparations intended for the oral route can contain, in addition to the bisphosphonic compounds, a disintegrating agent, a flow agent, a lubricant and any suitable bulk excipient.

Bulk excipients which can be used are lactose, cellulose and starches. Lubricants which can be used are stearic acid, magnesium stearate, L-leucine and, for example, glyceryl tribehenate. Disintegrating agents which can be used are sodium carboxymethyl starch, crosslinked sodium carboxymethylcellulose and, for example, crosslinked polyvinylpyrrolidone. Flow agents which can be used are pure silica or colloidal silicon dioxide.

The present invention also relates to instant-dissolving oral forms and to effervescent oral forms obtained by adding an effervescent couple to the composition according to the invention. Effervescent couples which can be used are tartaric acid and sodium bicarbonate or citric acid and sodium bicarbonate.

The invention also relates to instant-dissolving tablets, to effervescent tablets and to tablets covered with a coating. A composition containing sodium lauryl sulphate according to European patent EP 336 851 is particularly suitable.

The injectable preparations are prepared by mixing together one or more bisphosphonic acid derivatives with a pH regulator, a buffer, a suspending agent, a solubilizing agent, a stabilizer, a tonicity agent and/or a preserving agent, and by converting the mixture into an intravenous, subcutaneous, intra-muscular, intradermal or intra-articular injection according to a conventional process. Where necessary, the injectable preparations can be freeze-dried according to a conventional process.

Examples of suspending agents include methylcellulose, Polysorbate 80, hydroxyethylcellulose, acacia, powdered gum tragacanth, sodium carboxymethylcellulose and polyethoxylated sorbitan monolaurate.

Examples of solubilizing agents encompass castor oil solidified with polyoxyethylene, Polysorbate 80, nicotinamide, polyethoxylated sorbitan monolaurate, macrogol and the ethyl ester of castor oil fatty acid.

In addition, the stabilizer encompasses sodium sulphite, sodium metasulphite and ether, while the preserving agent encompasses methyl p-hydroxybenzoate, ethyl p-hydroxybenzoate, sorbic acid, phenol, cresol and chlorocresol.

An example of a tonicity agent is mannitol.

During the preparation of the injectable solutions or suspensions, it is desirable to take care to ensure that they are isotonic with the blood.

According to another of its aspects, the invention relates to the use of at least one bisphosphonic compound chosen from a bisphosphonic acid, a physiologically acceptable salt thereof and hydrates thereof, for the preparation of a formulation for increasing egg production and strengthening the shell of laid eggs.

The bisphosphonic compounds have the twofold function of improving the quality, and in particular the mechanical strength properties of the shells of laid eggs, and of increasing the production efficiency of the poultry.

It has been demonstrated that the administration of bisphosphonic compounds to poultry results in an increase in the total number of eggs laid during the laying period, as well as an increase in the average number of eggs laid per week during the laying period.

The magnitude of the effects obtained is at a maximum when the bisphosphonic compounds are administered before the onset of laying.

The plot of laying curves allows the effects obtained to be visualized; the laying curve represents the variations in the average number of eggs laid per week and per hen as a function of time, expressed in weeks. As a variant, the variations can be represented as a function of time, of the rate of laying, the rate of laying being defined as the ratio of the average number (n) of eggs laid per hen and per week to no (which is the theoretical value corresponding to one egg laid per day and per hen) multiplied by 100. In the present case, $n_o$ is 7.

The positive effects obtained are manifested by a lower slope of the laying curve and a higher laying peak (maximum number of eggs laid or maximum rate).

In parallel, higher mechanical strength of the shell is observed after the administration of the bisphosphonic compounds.

Advantageously, the administration of the bisphosphonic compounds is initiated before the average age of onset of laying, in the two months preceding the average age of onset of laying, preferably in the six weeks preceding the average age of onset of laying.

The duration of the treatment depends on the route of administration. The bisphosphonic compounds can be administered once only or at intervals (preferably at regular intervals) over the space of a few days or a few weeks.

Preferably, the administration of the bisphosphonic compounds is stopped at the onset of laying.

The rhythm of administration should also be chosen as a function of the route of administration, the nature of the bisphosphonic acid and the dose.

The administration can be carried out nasally, orally or parenterally. Via the oral or nasal route, it is preferred to administer the treatment repeatedly in a daily, two-daily or weekly rhythm or at regular intervals every 2 to 6 days. The dose per administration can be given in a single portion or fragmented over several hours, or alternatively continuously over a period of a few hours.

Via the parenteral route, the treatment can be administered either as a single injection or as repeated injections in a daily, two-daily or weekly rhythm or at regular intervals every 2 to 6 days. A preferred rhythm of treatment via the parenteral route is treatment in a single injection.

The recommended doses vary as a function of the compound chosen and the route of administration. Via the oral or nasal route, the doses per administration are between 0.01 and 100 mg/kg, preferably between 0.1 and 50 mg/kg. More particularly for tiludronate, the doses per administration are between 0.5 and 50 mg/kg, preferably between 1 and 20 mg/kg. Via the parenteral route, the doses per administration are between 0.001 and 50 mg/kg, preferably between 0.005 and 30 mg/kg. More particularly for tiludronate, the doses are between 0.1 and 50 mg/kg, preferably between 0.25 and 25 mg/kg.

EXAMPLE

A total number of 216 hens of ISA Brown strain between 15 and 17 weeks old was divided into 3 groups for the purpose of evaluating the effects on the production of eggs of a single subcutaneous administration of tiludronic acid, in the form of its sodium salt (disodium tiludronate).

Three doses were compared: 0, 1 and 10 mg/kg (corresponding amount of tiludronic acid/kg). The tiludronic acid was administered in the form of injectable aqueous solutions such that the volume injected per bird was 1 ml per kilo of live weight. The tiludronic acid solutions were thus concentrated to 0.1% and 1% for the doses of 1 and 10 mg/kg, respectively. The control group received a placebo corresponding to water for an injectable preparation. The injections were performed subcutaneously in the region above the superficial pectoral muscle.

The hens were housed in individual cages in the same building at controlled temperature and hygrometry. Each animal was identified by a number carried on a ring attached to a wing. They received the same standard feed for laying hens, freely throughout the duration of the study. Drinking water was also distributed freely.

The average age of onset of laying for the hens in this strain is 20 weeks, with extremes of between 18 and 23 weeks. Consequently, for the hens of this study, the average delay between the treatment and the age of onset of laying had to be from 3 to 5 weeks. The duration of the study was 40 weeks. At the end of the study, the hens were 55 weeks old.

One half of the total number of hens was sacrificed on laying the first egg, in order to carry out a histomorphometric examination. This examination was performed on one of the two tarsometatarsal bones.

The other half of the total number of hens was monitored in order to collect the following laying parameters: age on laying the first egg and total number of eggs laid up to 55 weeks old. For each group, the average number of eggs laid per hen and per week was calculated over the entire laying period and week by week, in order to establish the laying curves.

Moreover, an analysis of the mechanical strength of the shell and the thickness of the mineralized part of the shell was carried out using a sample of 12 hens at the following two dates of maturity: at 23 weeks old (i.e. at the start of laying) and at 54 weeks old. The strength of the shell was measured quantitatively by a technique of quasi-static compression of the eggshell. The thickness of the shell was measured from images obtained with an electron microscope.

At 55 weeks old, all the animals were sacrificed and a histomorphometric examination of one of the tarsometatarsal bones was performed under the same conditions as on the bones of the hens sacrificed on laying of the first egg.

The "age of onset of laying", "total number of eggs laid per hen", "number of eggs laid per hen and per week over the entire laying period", "mechanical strength of the shell", "thickness of the shell" and "medullary bone volume" criteria were compared by means of a single-factor variance analysis (dose factor).

1—Variation of the Average Age of Onset of Laying as a Function of the Dose of Tiludronic Acid Table 1 shows the average ages of laying of the first egg as a function of the dose of tiludronic acid for the entire number of hens monitored up to the age of 55 weeks.

TABLE 1

Age at the onset of laying (expressed in days) as a function of the dose of tiludronic acid (expressed in mg/kg)

| Dose of tiludronic acid (mg/kg) | 0 | 1 | 10 |
|---|---|---|---|
| Age of onset of laying (days) | 144.9 ± 8.1 | 148.3 ± 7.8 | 145.1 ± 8.8 |

For all of the hens, the average age of onset of laying is about 147 days (i.e. 21 weeks old), with extremes of between 124 days (i.e. 17.7 weeks) and 165 days (i.e. 23.6 weeks).

The average laying period was 34 weeks, irrespective of the group. The hens treated at a dose of 1 mg/kg started laying on average 3 days after the hens of the other 2 groups. However, the statistical analysis concludes that there is no significant difference (p=0.11) between the groups.

Thus, the treatment with tiludronic acid did not result in any change in the age of onset of laying.

2—Variation of the Total Number of Eggs Laid Over the Entire Laying Period as a Function of the Dose of Tiludronic Acid The total number of eggs laid over the entire laying period is given in Table 2.

TABLE 2

Total number of eggs laid per hen from the onset of laying up to 55 weeks old, as a function of the dose of tiludronic acid (expressed in mg/kg)

| Dose of tiludronic acid (mg/kg) | 0 | 1 | 10 |
|---|---|---|---|
| Average total number of eggs | 214.1 ± 14.0 | 221.6 ± 11.2 | 219.8 ± 12.6 |

A difference appears in the average number of eggs laid per hen between the control group and the two groups treated with tiludronic acid: on average, the treated hens laid between 5.7 and 7.5 more eggs. The statistical analysis reveals a significant difference at the 5% threshold between the 3 groups (p=0.03). A 2-by-2 analysis demonstrates that the total number of eggs laid per hen in the group treated at a dose of 1 mg/kg is significantly higher than the total number of eggs laid per hen in the control group.

The treatment with tiludronic acid thus resulted in an increase in the number of eggs laid over the laying period.

3—Variation in the Average Number of Eggs Laid per Week as a Function of the Dose of Tiludronic Acid Table 3, relating to the average number of eggs laid per week, confirms this observation.

TABLE 3

Average number of eggs laid per hen and per week from the onset of laying up to 55 weeks old, as a function of the dose of tiludronic acid (expressed in mg/kg)

| Dose of tiludronic acid (mg/kg) | 0 | 1 | 10 |
|---|---|---|---|
| Average number/week | 6.23 ± 0.38 | 6.53 ± 0.27 | 6.39 ± 0.34 |

The statistical analysis reveals a highly significant difference (p=0.001) between the 3 groups, the group treated at a dose of 1 mg/kg having laid more eggs on average per week of laying than the control group.

4—Laying Curve

The laying curves constructed from the average number of eggs laid per hen and per week next expressed as a percentage relative to the theoretical value of 7 (i.e. one egg laid per day and per hen each week) are presented in FIG. 1. FIG. 2. is a magnification of the upper zone of the laying curve. The laying peak is higher in the treated groups than in the control group. The natural decrease in the rate of laying over time is slowed down in the treated hens, in particular at a dose of 1 mg/kg, compared with the controls. The slope of the laying curve thus appears to be substantially smaller in the treated groups. This difference in slope is the cause of the differences demonstrated above regarding the total number of eggs laid and the average number of eggs laid per week.

5—Mechanical Strength of the Eggshell

The quality criteria of the shells of the eggs produced in this study are reported in Tables 4 and 5.

Table 4 shows the values obtained in the mechanical strength test.

TABLE 4

Mechanical strength (expressed in N) of the shell of
the eggs taken from a sample of 12 hens at 23 and 54
weeks old, as a function of the dose of tiludronic
acid (expressed in mg/kg)

| Dose of tiludronic acid (mg/kg) | 0 | 1 | 10 |
|---|---|---|---|
| Strength at 23 weeks | 37.2 ± 4.1 | 39.3 ± 5.2 | 41.5 ± 6.3 |
| Strength at 54 weeks | 21.5 ± 10.1 | 28.3 ± 4.9 | 30.3 ± 6.1 |

The results suggest a relationship between the dose and the effect, both on the eggs taken at the start of laying and at 54 weeks old. The difference between the control group and the treated groups is more pronounced at 54 weeks than at 23 weeks. This indicates that the loss of mechanical strength of the eggshells, which is a natural process which develops gradually as the laying period progresses, is lower in the animals treated with tiludronic acid (about −28% for the two groups treated between the two maturity dates of measurement) than in the untreated controls (−42%). The statistical analysis does not reveal any significant differences at the 5% threshold; this can be explained by the relatively high individual variability which characterizes this parameter.

Examination of the "thickness of the mineralized part of the shell" parameter presented in Table 5 makes it possible to conclude in the same sense as the above criterion, even though the statistical analysis does not reveal any significant differences at the 5% threshold. The shell is seen to be thicker in the animals treated with tiludronic acid; the effect is more pronounced in the hens treated at a dose of 10 mg/kg, in particular at 54 weeks old. Moreover, there is good correlation between the mechanical strength of the shell and the thickness of the mineralized part: the greater the thickness, the higher the strength.

TABLE 5

Thickness of the mineralized part of the shell
(expressed in mm) of eggs taken from a sample of 12
hens at 23 and 54 weeks old, as a function of the dose
of tiludronic acid (expressed in mg/kg)

| Dose of tiludronic acid (mg/kg) | 0 | 1 | 10 |
|---|---|---|---|
| Thickness at 23 weeks | 0.255 ± 0.028 | 0.256 ± 0.025 | 0.272 ± 0.013 |
| Thickness at 54 weeks | 0.249 ± 0.015 | 0.267 ± 0.026 | 0.273 ± 0.021 |

The two parameters analyzed previously are good indicators of the quality of the shell. The results obtained in this study thus suggest very strongly that tiludronic acid induces an improvement in the quality of the eggshell.

6—Volume of the Tarsometatarsal Medullary Bone

At the onset of laying, the medullary bone volumes are relatively small, with no difference between the groups. This corresponds to the recent formation of medullary bone, which begins about 2 weeks before the onset of laying, with high individual variability.

At 55 weeks old too, there is no significant difference between the groups; this can also be explained by the high individual variability. However, it appears that the development of medullary bone is greater in the animals which received the tiludronate than in the control animals. Whereas, in the latter animals, the medullary bone volume was multiplied on average by a factor of 6, the multiplication factor is 9 at a dose of 1 mg/kg and 13 at a dose of 10 mg/kg.

TABLE 6

Volume of medullary bone (expressed in %) of
the tarsometatarsal bone at the onset of laying and at
55 weeks old, as a function of the dose of tiludronic
acid (expressed in mg/kg)

| Dose of tiludronic acid (mg/kg) | 0 | 1 | 10 |
|---|---|---|---|
| At the onset of laying | 0.53 ± 0.76 | 0.31 ± 0.53 | 0.26 ± 0.33 |
| At 55 weeks old | 2.93 ± 2.03 | 2.75 ± 2.72 | 3.53 ± 3.04 |

These results suggest a beneficial effect of tiludronic acid on the medullary bone remodelling. This observation agrees with the beneficial effect reported previously regarding egg production and the quality of the eggshell. However, in the current state of knowledge of the mode of action of bisphosphonic acid derivatives, this beneficial effect was unexpected.

What is claimed is:

1. Process for increasing egg production and strengthening eggshells in poultry, which comprises the administration to the poultry animal of at least one bisphosphonic compound selected from the group consisting of:
   a) 4-chlorophenylthiomethylenebisphosphonic acid, a physiologically acceptable salt thereof, hydrates thereof, and mixtures thereof and
   b) compound of formula I:

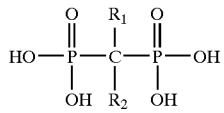

in which:
   $R_1$ is a halogen atom or a $(C_1-C_{12})$ alkyl group which is optionally substituted with one or more halogen atoms and
   $R_2$ is a thiol substituted with $(C_6-C_{12})$aryl or $(C_4-C_{10})$ heteroaryl optionally substituted with one or more thiol and/or halogen groups,
wherein the at least one bisphosphonic compound is administered at a dose sufficient for inhibiting bone resorption and is administered within two months before the age of onset of laying.

2. Process according to claim 1, wherein the bisphosphonic compound is 4-chlorophenylthiomethylenebisphosphonic acid, a physiologically acceptable salt thereof, hydrates thereof, and mixtures thereof.

3. Process according to claim 2, wherein the animal is poultry which produces eggs intended for consumption.

4. Process according to claim 3, wherein the poultry is chosen from hens, ducks and quails.

5. Process according to claim 2, wherein the administration is carried out via the oral, parenteral or nasal route.

6. Process according to claim 5, wherein a dose administered via the oral or nasal route is between about 0.01 and 100 mg/kg of body weight.

7. Process according to claim 5, wherein a dose administered via the parenteral route is between about 0.0005 and 30 mg/kg of body weight.

8. Process according to claim 2, wherein the administration of the bisphosphonic compound is initiated in the six weeks preceding the age of onset of laying.

9. Process according to claim 2, wherein the bisphosphonic compound is administered once only or at intervals before the onset of laying.

* * * * *